(12) United States Patent
Velis

(10) Patent No.: US 10,500,342 B2
(45) Date of Patent: Dec. 10, 2019

(54) COLD SLURRY SYRINGE

(71) Applicant: Christopher J. P. Velis, Cambridge, MA (US)

(72) Inventor: Christopher J. P. Velis, Cambridge, MA (US)

(73) Assignee: MIRAKI INNOVATION THINK TANK LLC, Cambridge, MA (US)

(*) Notice: Subject to any disclaimer, the term of this patent is extended or adjusted under 35 U.S.C. 154(b) by 137 days.

(21) Appl. No.: 15/682,234

(22) Filed: Aug. 21, 2017

(65) Prior Publication Data
US 2019/0054242 A1    Feb. 21, 2019

(51) Int. Cl.
*A61M 5/31* (2006.01)
*A61M 5/315* (2006.01)
*A61M 5/20* (2006.01)

(52) U.S. Cl.
CPC ...... *A61M 5/3134* (2013.01); *A61M 5/31511* (2013.01); *A61M 5/31596* (2013.01); *A61M 2005/2026* (2013.01)

(58) Field of Classification Search
CPC .. A61M 5/3134; A61M 5/31596; A61M 5/32; A61M 5/2066; A61M 5/31583;
(Continued)

(56) References Cited

U.S. PATENT DOCUMENTS 3,767,085 A * 10/1973 Cannon .............. A61C 9/0026
                                                       222/82
4,986,079 A      1/1991 Koseki et al.
(Continued)

FOREIGN PATENT DOCUMENTS

CN    103110473 A    5/2013
CN    105640706 A    6/2016
(Continued)

OTHER PUBLICATIONS

Ash, 2003, Chronic peritoneal dialysis catheters: overview of design, placement, and removal procedures, Int Nephrol Dialysis 16(4):323-34.
(Continued)

*Primary Examiner* — Bhisma Mehta
*Assistant Examiner* — Nidah M Hussain
(74) *Attorney, Agent, or Firm* — Brown Rudnick LLP; Thomas C. Meyers

(57) ABSTRACT

A cold slurry syringe with enhanced features is provided for delivering a cold slurry into the human body. The syringe includes a syringe body for holding a volume of cold slurry, a plunger that slides within the syringe body for ejecting the cold slurry, and a tapered syringe head for delivering an even flow of cold slurry. An agitator can be added to keep the cold slurry from agglomerating and clogging the syringe. Insulation added around the syringe can keep the cold slurry from melting too quickly. A ball screw drive can be added to provide a smooth and consistent application of pressure as the cold slurry is delivered. The cold slurry flow can be enhanced by adding a streamline flow feature that reduces the occurrence of eddies or swirls inside the syringe. This feature can also help maintain the composition and consistency of the cold slurry.

16 Claims, 10 Drawing Sheets

(58) Field of Classification Search
CPC .......... A61M 3/005; A61M 2005/3152; A61K 8/044; B01F 15/02; B01F 15/0266; B01F 15/0273; B01F 15/0278; B01F 15/0279
USPC .......................................... 604/197; 366/189
See application file for complete search history.

(56) References Cited

U.S. PATENT DOCUMENTS

| | | |
|---|---|---|
| 5,143,063 A | 9/1992 | Fellner |
| 5,507,790 A | 4/1996 | Weiss |
| 5,769,879 A | 6/1998 | Richards et al. |
| 6,032,675 A | 3/2000 | Rubinsky |
| 6,041,787 A | 3/2000 | Rubinsky |
| 6,244,052 B1 | 6/2001 | Kasza |
| 6,300,130 B1 | 10/2001 | Toner et al. |
| 6,324,863 B1 | 12/2001 | Henry |
| 6,334,328 B1 | 1/2002 | Brill |
| 6,403,376 B1 | 6/2002 | Toner et al. |
| 6,413,444 B1 | 7/2002 | Kasza |
| 6,430,957 B1 | 8/2002 | Inada et al. |
| 6,475,212 B2 | 11/2002 | Dobak, III et al. |
| 6,547,811 B1 | 4/2003 | Becker et al. |
| 6,673,607 B2 | 1/2004 | Toner et al. |
| 6,849,072 B2 | 2/2005 | Lee et al. |
| 6,962,601 B2 | 11/2005 | Becker et al. |
| 7,118,591 B2 | 10/2006 | Frank et al. |
| 7,367,341 B2 | 5/2008 | Anderson et al. |
| 7,389,653 B2 | 6/2008 | Kasza et al. |
| 7,422,601 B2 | 9/2008 | Becker et al. |
| 7,507,234 B2 | 3/2009 | Utley et al. |
| 7,603,868 B2 | 10/2009 | Sveinsson |
| 7,681,411 B2 | 3/2010 | DiLorenzo |
| 7,713,266 B2 | 5/2010 | Elkins et al. |
| 7,854,754 B2 | 12/2010 | Ting et al. |
| 8,117,854 B2 | 2/2012 | Lampe et al. |
| 8,192,474 B2 | 6/2012 | Levinson |
| 8,275,442 B2 | 9/2012 | Allison |
| 8,285,390 B2 | 10/2012 | Levinson et al. |
| 8,298,216 B2 | 10/2012 | Burger et al. |
| 8,337,539 B2 | 12/2012 | Ting et al. |
| 8,505,315 B2 | 8/2013 | Kasza et al. |
| 8,523,927 B2 | 9/2013 | Levinson et al. |
| 8,603,073 B2 | 12/2013 | Allison |
| 8,608,696 B1 | 12/2013 | DiMeo et al. |
| 8,676,338 B2 | 3/2014 | Levinson |
| 8,702,774 B2 | 4/2014 | Baker et al. |
| 8,808,241 B2 | 8/2014 | DiMeo et al. |
| 8,840,608 B2 | 9/2014 | Anderson et al. |
| 8,936,577 B2 * | 1/2015 | Lee ..................... A61M 5/3129 604/191 |
| 8,974,451 B2 | 3/2015 | Smith |
| 9,016,925 B2 * | 4/2015 | Faccioli .............. B01F 11/0054 366/130 |
| 9,044,212 B2 | 6/2015 | LePivert |
| 9,078,634 B2 | 7/2015 | Gonzales et al. |
| 9,132,031 B2 | 9/2015 | Levinson et al. |
| 9,314,368 B2 | 4/2016 | Allison et al. |
| 9,345,526 B2 | 5/2016 | Elkins et al. |
| 9,375,345 B2 | 6/2016 | Levinson et al. |
| 9,398,930 B2 | 7/2016 | Leung et al. |
| 9,408,745 B2 | 8/2016 | Levinson et al. |
| 9,522,031 B2 | 12/2016 | Anderson et al. |
| 9,545,523 B2 | 1/2017 | Nanda |
| 9,585,687 B2 | 3/2017 | Tenenbaum et al. |
| 9,649,220 B2 | 5/2017 | Anderson et al. |
| 9,655,770 B2 | 5/2017 | Levinson et al. |
| 9,656,056 B2 | 5/2017 | Boyden et al. |
| 2002/0107199 A1 | 8/2002 | Walker |
| 2003/0032996 A1 | 2/2003 | Hallman |
| 2005/0203598 A1 | 9/2005 | Becker et al. |
| 2005/0251120 A1 | 11/2005 | Anderson et al. |
| 2006/0036302 A1 | 2/2006 | Kasza et al. |
| 2006/0161232 A1 | 7/2006 | Kasza et al. |
| 2007/0010861 A1 | 1/2007 | Anderson et al. |
| 2007/0056313 A1 | 3/2007 | Kasza et al. |
| 2007/0106247 A1 | 5/2007 | Burnett et al. |
| 2007/0198071 A1 | 8/2007 | Ting et al. |
| 2007/0255362 A1 | 11/2007 | Levinson et al. |
| 2007/0270925 A1 | 11/2007 | Levinson |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0236186 A1 | 10/2008 | Kasza et al. |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0118722 A1 | 5/2009 | Ebbers et al. |
| 2009/0125087 A1 | 5/2009 | Becker et al. |
| 2009/0149929 A1 | 6/2009 | Levinson et al. |
| 2009/0255276 A1 | 10/2009 | Kasza et al. |
| 2010/0036295 A1 | 2/2010 | Altshuler et al. |
| 2010/0081971 A1 | 4/2010 | Allison |
| 2010/0152824 A1 | 6/2010 | Allison |
| 2010/0152880 A1 | 6/2010 | Boyden et al. |
| 2010/0280582 A1 | 11/2010 | Baker et al. |
| 2011/0066216 A1 | 3/2011 | Ting et al. |
| 2011/0238050 A1 | 9/2011 | Allison et al. |
| 2011/0238051 A1 | 9/2011 | Levinson et al. |
| 2011/0300079 A1 | 12/2011 | Martens et al. |
| 2012/0000217 A1 | 1/2012 | Gudnason |
| 2012/0022518 A1 | 1/2012 | Levinson |
| 2012/0101478 A1 * | 4/2012 | Stroumpoulis ........ A61M 3/005 604/518 |
| 2012/0239123 A1 | 9/2012 | Weber et al. |
| 2013/0066309 A1 | 3/2013 | Levinson |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0158440 A1 | 6/2013 | Allison |
| 2013/0158636 A1 | 6/2013 | Ting et al. |
| 2013/0190744 A1 | 7/2013 | Avram et al. |
| 2013/0245731 A1 | 9/2013 | Allison |
| 2013/0253496 A1 | 9/2013 | Anderson et al. |
| 2014/0005760 A1 | 1/2014 | Levinson et al. |
| 2014/0067025 A1 | 3/2014 | Levinson et al. |
| 2014/0091113 A1 | 4/2014 | Brewster et al. |
| 2014/0200511 A1 | 7/2014 | Boyden et al. |
| 2014/0257443 A1 | 9/2014 | Baker et al. |
| 2014/0277219 A1 | 9/2014 | Nanda |
| 2014/0277302 A1 | 9/2014 | Weber et al. |
| 2014/0303696 A1 | 10/2014 | Anderson et al. |
| 2014/0303697 A1 | 10/2014 | Anderson et al. |
| 2014/0316393 A1 | 10/2014 | Levinson |
| 2014/0358079 A1 | 12/2014 | Fischell et al. |
| 2015/0112195 A1 | 4/2015 | Berger et al. |
| 2015/0216816 A1 | 8/2015 | O'Neil et al. |
| 2015/0297246 A1 | 10/2015 | Patel |
| 2015/0328077 A1 | 11/2015 | Levinson |
| 2015/0328405 A1 * | 11/2015 | Metzner ................ A61M 5/20 604/143 |
| 2015/0342780 A1 | 12/2015 | Levinson et al. |
| 2015/0343156 A1 | 12/2015 | Fischell et al. |
| 2016/0051401 A1 | 2/2016 | Yee et al. |
| 2016/0058956 A1 | 3/2016 | Cohn et al. |
| 2016/0089550 A1 | 3/2016 | DeBenedictis et al. |
| 2016/0112195 A1 | 4/2016 | Jochheim et al. |
| 2016/0128767 A1 | 5/2016 | Azamian et al. |
| 2016/0175141 A1 | 6/2016 | Wu et al. |
| 2016/0242661 A1 | 8/2016 | Fischell et al. |
| 2016/0317621 A1 | 11/2016 | Bright |
| 2016/0354137 A1 | 12/2016 | Fischell et al. |
| 2016/0354237 A1 | 12/2016 | Gonzales et al. |
| 2017/0105869 A1 | 4/2017 | Frangineas, Jr. |
| 2017/0136237 A1 | 5/2017 | Eckhouse et al. |
| 2017/0143538 A1 | 5/2017 | Lee et al. |
| 2017/0164965 A1 | 6/2017 | Chang et al. |
| 2017/0202613 A1 | 7/2017 | Pellegrino et al. |
| 2017/0246032 A1 | 8/2017 | Gonzales et al. |
| 2017/0274011 A1 * | 9/2017 | Garibyan ............. A61K 33/00 |
| 2017/0325992 A1 | 11/2017 | DeBenedictis et al. |

(56) References Cited

U.S. PATENT DOCUMENTS

FOREIGN PATENT DOCUMENTS

| EP | 0418979 A2 | 3/1991 | | |
|---|---|---|---|---|
| WO | 2016/033380 A1 | 3/2016 | | |
| WO | 2016/033384 A1 | 3/2016 | | |
| WO | 2016/090175 A1 | 6/2016 | | |
| WO | WO-2017147367 A1 | * | 8/2017 | ............. A61B 18/02 |
| WO | WO 2017147367 A1 | * | 8/2017 | |
| WO | 2017/196548 A1 | 11/2017 | | |

OTHER PUBLICATIONS

Brink, 2008, Abdominoplasty with direct resection of deep fat, Plast Reconstructive Surg 123(5):1597-1603.

Ding, 2008, The association between non-subcutaneous adiposity and calcified coronary plaque: A substudy of the multi-ethnic study of atherosclerosis, Am J Clin Nutr 88(3):645-650.

Fox, 2007, Abdominal visceral and subcutaneous adipose tissue compartments—association with metabolic risk factors in the Framingham heart study, Circulation 116:39-48.

Garaulet, 2006, Relationship between fat cell size and number and fatty acid composition in adipose tissue from different fat depots in overweight/obese humans, Int J Obes 30(6):899-905.

Gradinger, 2005, Abdominoplasty, Chapter 83, pp. 2935-3026, in the art of aesthetic surgery: principles & techniques, Nahai, Ed., Quality Med Pub, St. Louis Mo. (92 pages).

International Search Report and Written Opinion dated Apr. 12, 2011, for International Application No. PCT/US11/24766, filed Feb. 14, 2011 (11 pages).

Laven, 2006, A pilot study of ice-slurry application for inducing laparoscopic renal hypothermia, BJU Int 99:166-70.

Laverson, 2006, Improving abdominoplasty results: reconstruction of the linea alba sulcus by direct excision, Aesthetic Surg J 26:682-6.

Stevens, 2014, "Does cryolipolysis lead to skin tightening? A first report of cryodermadstringo", Aesth Surg J 34(6):NP32-NP34.

Yamamoto, 2010, Adipose depots possess unique developmental gene signatures, Obesity 18(5):872-78.

* cited by examiner

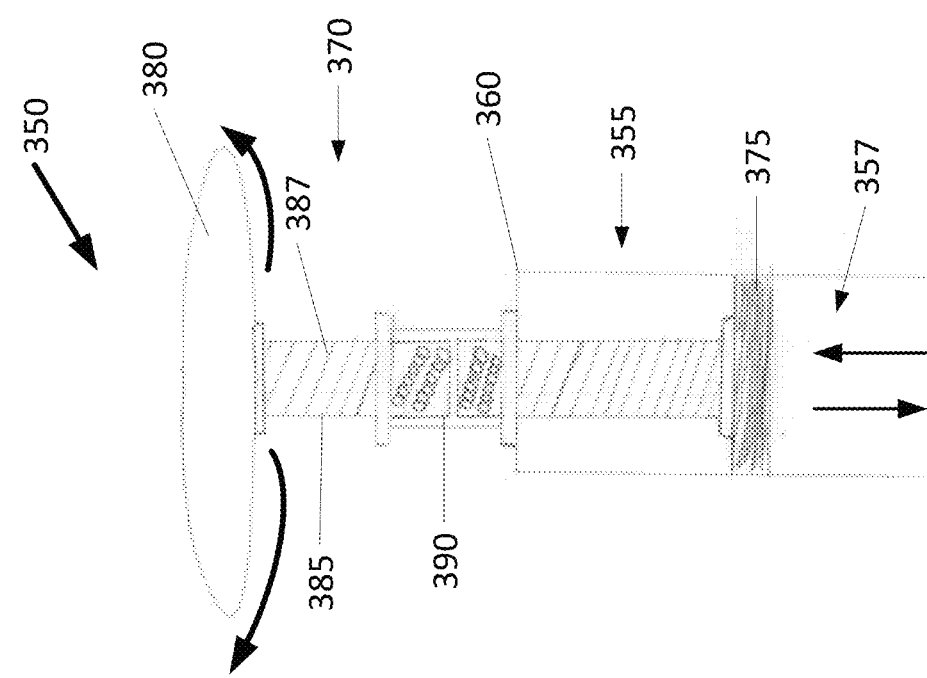
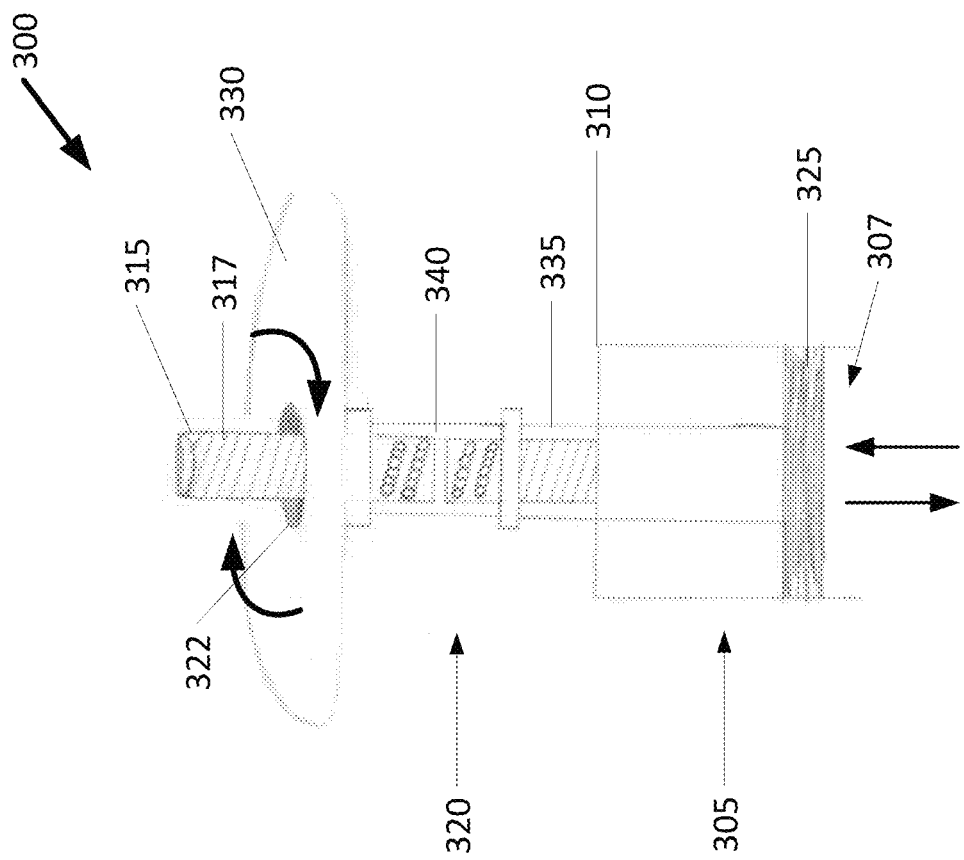
FIG. 5B
FIG. 5A

COLD SLURRY SYRINGE

CROSS REFERENCE TO RELATED APPLICATIONS

None.

BACKGROUND

A syringe is a pump consisting of a plunger that fits tightly in a cylindrical tube. The plunger can be pulled and pushed along inside the tube allowing the syringe to take in and expel a liquid through an orifice at the open end of the tube. The open end can be fitted with a hypodermic needle, a nozzle or tubing.

SUMMARY

The internal deposition of cold slurry has many potential clinical benefits. The present invention relates to the delivery of cold slurry to internal tissues and organs as a therapy for a variety of health conditions. For example, cold slurry is delivered at or near adipose tissue, colonic tissue, or abdominal tissue. The cooling effect of the cold slurry on those tissues or others stimulates thermogenesis in brown adipose tissue and increases general metabolic activity. As such, cold slurry therapy is useful to treat obesity, to reduce adipose tissue, and to treat metabolic conditions associated therewith. In another example, cold slurry is delivered at or near internal tissue injured by trauma or disease. The cooling effect of the cold slurry on the injured tissue reduces inflammation which, in turn, reduces pain and promotes healing.

The application of cold slurry is also useful to treat a number of muscular and neurological disorders as well as to treat pain. For example, the cooling effect of cold slurry delivered at or near a nerve reduces the neuronal activity, thereby reducing spasms or pain. The cooling effect of cold slurry on tissue is also used to reduce or remove tissue, for example, to treat fibroadenomas or scar tissue.

One approach to delivering cold slurry is to inject the cold slurry under a patient's skin using a syringe 10 shown in FIG. 1. The syringe 10 includes a syringe body 15 having a first end 20 and a second end 25. The syringe body 15 defines a cavity 30 for holding cold slurry 35. Extending from the first end 20, there is an outlet 40 defining a passageway that is in fluid communication with the cavity 30. The outlet serves as a port for discharging the cold slurry 35 from the cavity 30 or a cool fluid that transitions to a slurry. Extending from the outlet 40 there is hollow needle 45 for piercing through the patient's skin and providing a conduit from delivering the cold slurry 35 at or near a tissue the targeted for the cold slurry treatment.

The syringe 10 further includes a plunger 50 that slides within the cavity 30 between the first end 20 and the second end 25. At one end, facing the first end 20 of the syringe body 15, the plunger 50 includes a stopper 55 for pushing the cold slurry 35. A stem 60 extends from the stopper 55 towards the second end 25 and terminates at a flange 70. In use, to deliver the cold slurry 35 to a target tissue, a clinician pierces the patient's skin with the needle 45 and advances the needle 45 to a location at or near the target tissue. The clinician then pressed down on the syringe flange 70, which in turn delivers the cold slurry 35 from the cavity 30 through the outlet 40 and out the needle 45 to the target tissue.

The cold slurry is preferably kept at a proper treatment temperature. Depending on the tissue being treated, cold slurry temperature ranges from about 10° C. to about −50° C. Cold slurry melts quickly, so temperature must be maintained, especially when multiple injections are used.

A cold slurry syringe according to the invention has enhanced features for delivering a cold slurry into the human body. A syringe of the invention includes a syringe body for holding a volume of cold slurry (or a cool fluid that transitions to a cold slurry), a plunger that slides within the syringe body for ejecting the cold slurry, and a tapered syringe head for delivering an even flow of cold slurry. The taper prevents, or assists in preventing, clogging or phase change of the material in the syringe. An agitator can be added to keep the cold slurry from agglomerating and clogging the cold slurry syringe. The agitator can have many forms such as vibration, rotation, and use of augers. Insulation added around the cold slurry syringe can keep the cold slurry from melting too quickly. A ball screw drive, or other mechanism for controlling content pressure and/or flow from the device, can be added to provide a smooth and consistent application of pressure as the cold slurry is delivered. The cold slurry flow can be enhanced by adding a streamline flow feature that reduces the occurrence of eddies or swirls inside the syringe. This feature helps maintain the composition and consistency of the cold slurry.

One aspect of the invention is a device comprising a syringe body having a first end, a second end, and a longitudinal axis extending through the first and second ends. The syringe body further includes an interior lumen defined by an interior wall of the syringe body. The interior lumen is configured to receive and contain a volume of cold slurry. In some examples, the cold slurry can be made inside the syringe. In such examples, the interior lumen receives a cool fluid where it is cooled down to become a cold slurry. The device further has a plunger that is slideably movable within the interior lumen between the first and second ends along the longitudinal axis. The plunger includes a stopper and a stem extending from the stopper.

The device further has a syringe head extending from the first end of the syringe body along the longitudinal axis. The syringe head includes an inlet defining a first passageway in fluid communication with the interior lumen of the syringe body. The first passageway has a first diameter that is about the same as a diameter of the interior lumen. The syringe head further includes an outlet spaced a predetermined distance from the inlet along the longitudinal axis. The outlet defines a second passageway in fluid communication with the outside to serve as an exit for delivering cold slurry. The second passageway has a second diameter smaller than the first diameter. Extending between the inlet and outlet there is a reducer. The reducer defines a third passageway in fluid communication with the first and second passageways. The third passageway has a third diameter tapering from the first diameter to the second diameter.

BRIEF DESCRIPTION OF DRAWINGS

FIGS. 5A and 5B are views of example cold slurry syringes each with a ball screw drive for moving a plunger within a syringe body and delivering cold slurry.

DETAILED DESCRIPTION

The present invention provides a cold slurry syringe with enhanced features for delivering cold slurry into the human body. A cold slurry syringe of the invention includes a syringe body for holding a volume of cold slurry, a plunger that slides within the syringe body for ejecting the cold slurry, and a tapered syringe head for delivering an even flow of cold slurry. An agitator can be added to the cold slurry syringe to keep the cold slurry from agglomerating and clogging the cold slurry syringe. A ball screw drive, or other mechanism for controlling flow of pressure, can be added to the cold slurry syringe to provide a smooth and consistent application of pressure as the cold slurry is delivered. Insulation added around the cold slurry syringe can keep the cold slurry from melting too quickly. The flow of cold slurry can be enhanced by adding a streamline flow feature to the cold slurry syringe that can reduce eddies or swirls from occurring inside the cold slurry syringe. Examples of the aforementioned enhancements and others are now described in greater detail below.

Figure 1:
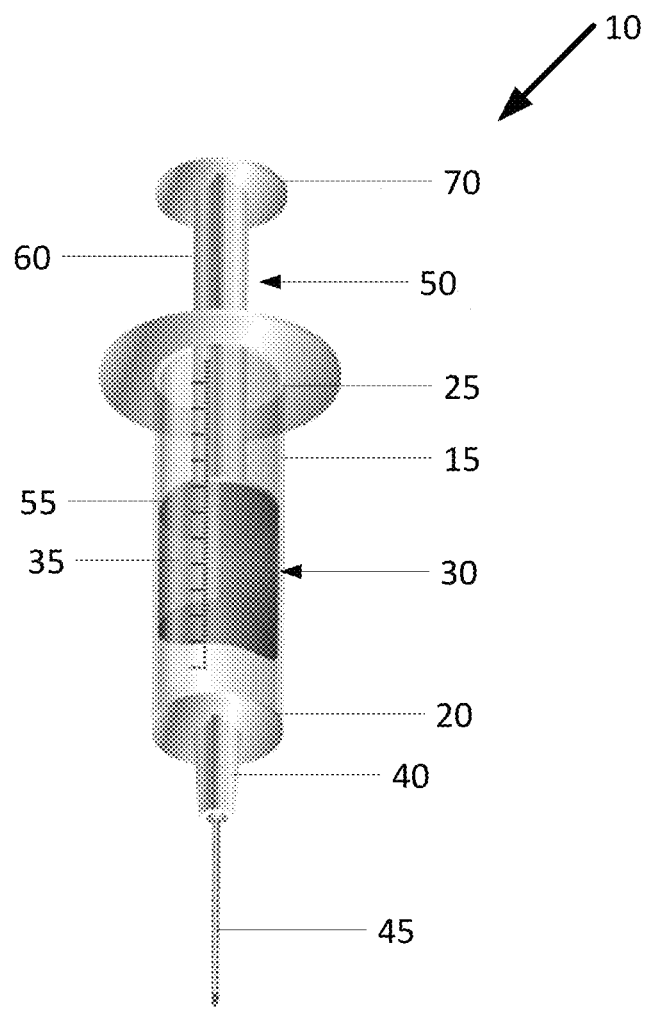
FIG. 1 shows a syringe for delivering cold slurry.
Figure 2A:
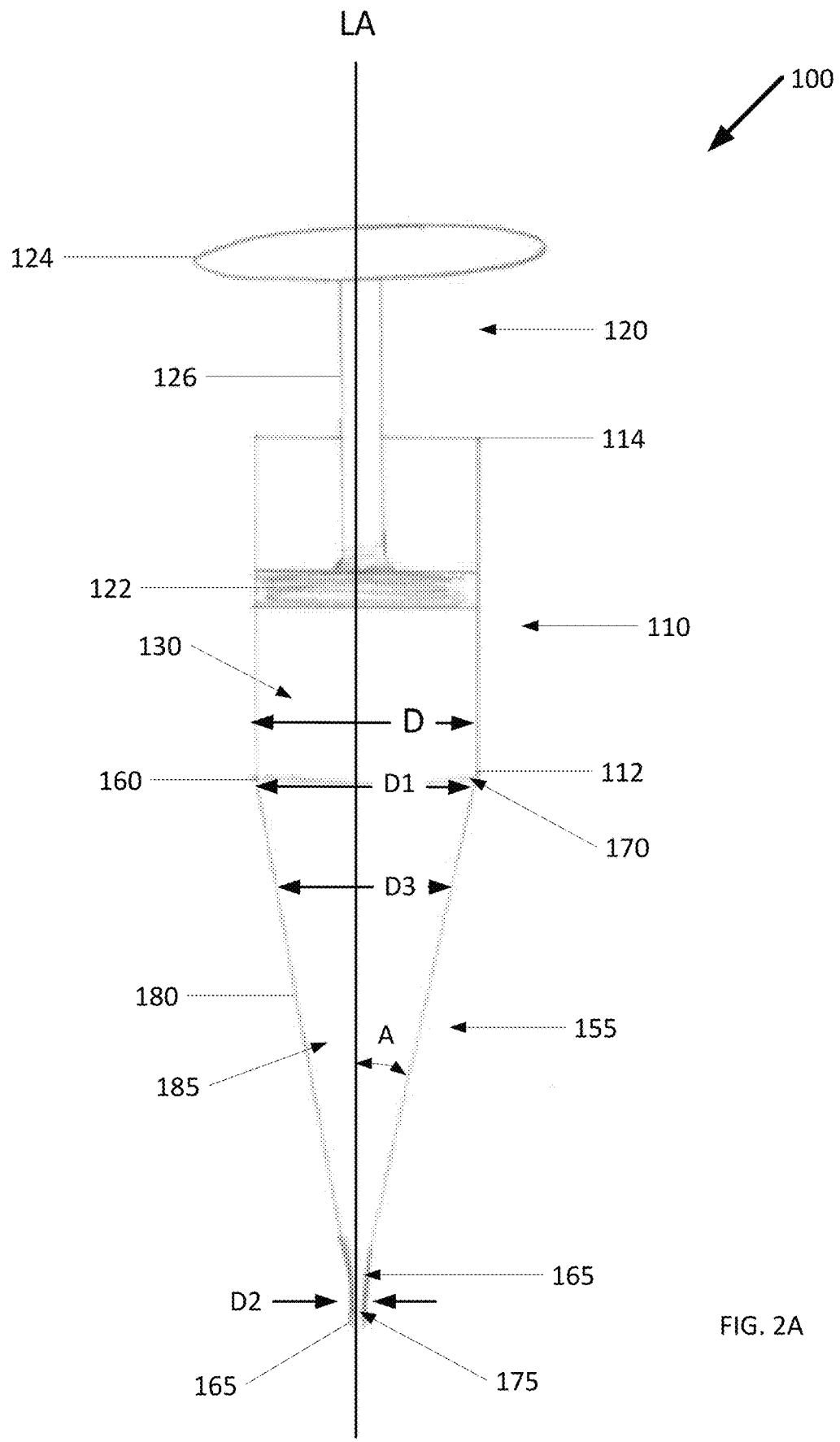
FIG. 2A is a cross section view of an example cold slurry syringe.

FIG. 2 shows an example cold slurry syringe 100. The cold slurry syringe 100 includes a syringe body 110 having a first end 112, a second end 114, and a longitudinal axis LA extending through the first end 112 and the second end 114. The cold slurry syringe 100 also includes an interior lumen 130 defined by the interior wall of the syringe body 110 to receive and contain cold slurry.

The cold slurry syringe 100 further includes a plunger 120 at least partially disposed within the interior lumen 130. The plunger 120 is configured to move in and out of the syringe body 110 between the first end 112 and the second end 114. The plunger 120 includes a stopper 122, a plunger head 124, and a stem 126 extending between the stopper 122 and the plunger head 124 along the longitudinal axis LA. The stopper 122 and the plunger head 124 are spaced apart at a predetermined distance.

The syringe body 110 can be made of any type of biocompatible pharmacologically inert material suitable for use in containing and supplying fluids to be provided within a human body. Exemplary materials for the syringe body 110 include plastic, such as polyethylene or polypropylene, and glass. The cold slurry syringe 100 can be any size that is suitable to hold one or more aliquots of cold slurry for delivery to the target tissue. The volume capacity of the cold slurry syringe 100 is typically between 1 ml and 60 ml, although capacity outside of those volumes is also contemplated.

The cold slurry syringe 100 further includes a syringe head 155 extending from the first end 112 of the syringe body 110 along the longitudinal axis LA. The syringe head 155 has an inlet 160 and an outlet 165 spaced a predetermined distance from the inlet 160 along the longitudinal axis LA. The inlet 160 defines a first passageway 170 in fluid communication with the interior lumen 130. The interior lumen 130 has a diameter D and the first passageway 170 has a first diameter D1 that is about the same as the interior lumen diameter D. The outlet 165 defines a second passageway 175 in fluid communication with the outside environment and serves as an exit for delivering the cold slurry. The second passageway 175 has a second diameter D2 that is smaller than the first diameter D1.

Extending between the inlet 160 and outlet 165, there is a reducer 180 defining a third passageway 185 in fluid communication with the first passageway 170 and the second passageway 175. The third passageway 185 has a third diameter that tapers from the first diameter D1 to the second diameter D2. This arrangement of passageways provides a smooth transition that allows the cold slurry to flow evenly from the interior lumen 130 through the inlet 160 and out the outlet 165. Reducing turbulence in the cold slurry flow can reduce the possibility that ice particles making up the cold slurry will aggregate and clog the cold slurry syringe 100.

Figure 2B:
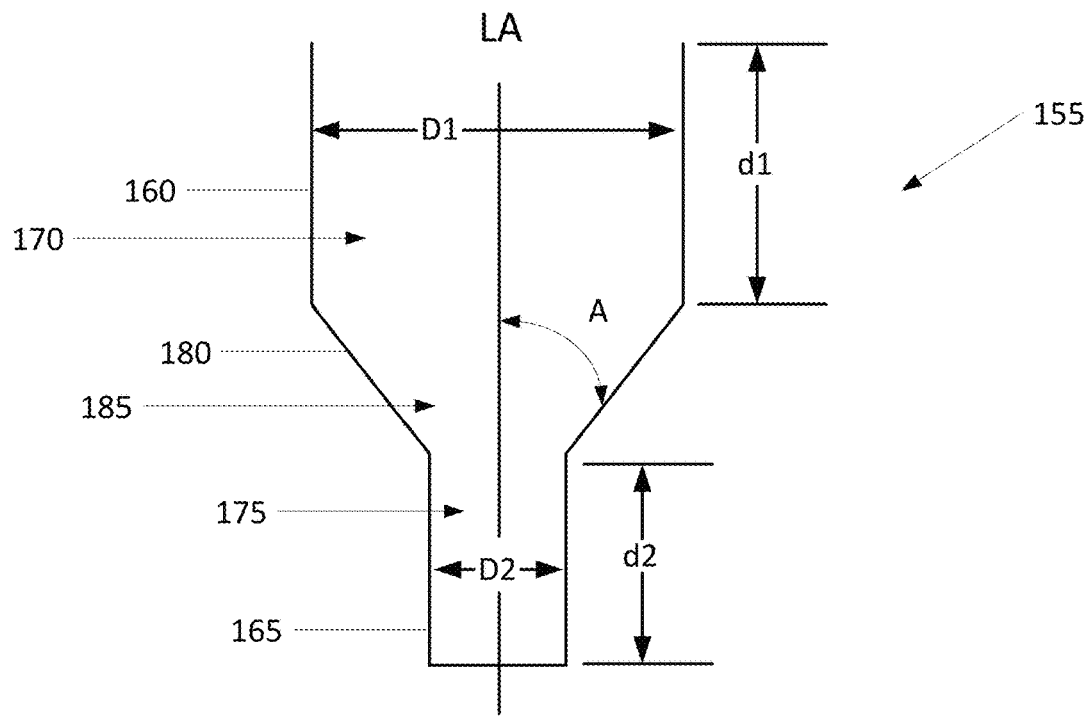
FIG. 2B is a cross section view of an example syringe head.
Figure 2C:
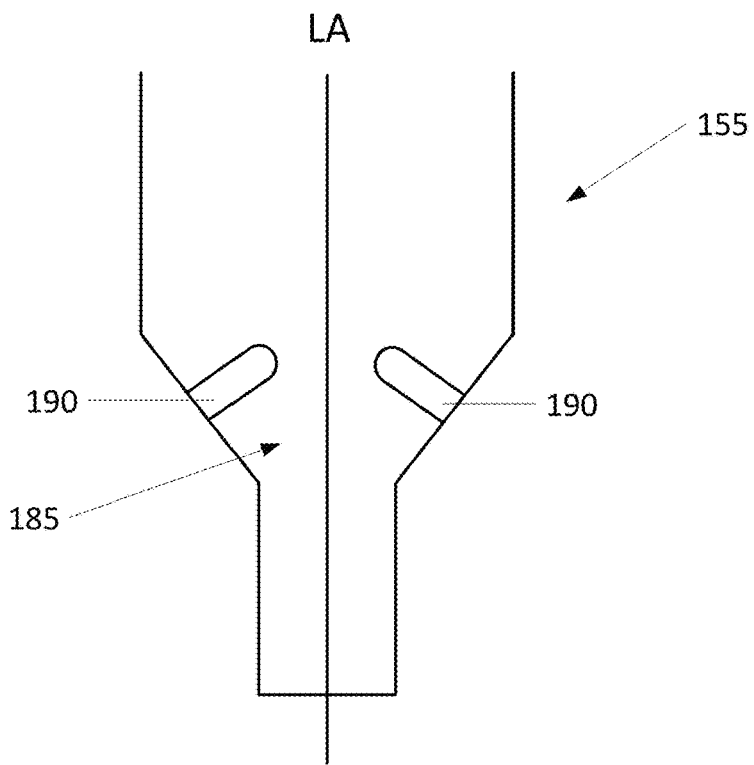
FIG. 2C is a cross section view of an example syringe head with projections.

The configuration and geometry of the syringe head 155 can be changed to alter the flow characteristics of the cold slurry. For example, FIG. 2B shows an example of the syringe head in which the inlet 160 and the outlet 165 have walls that are generally parallel with the longitudinal axis LA. In this example, the first diameter D1 extends over a distance d1 such that the cold slurry travels this distance through the first passageway 170 before the cold slurry flow is narrowed by the reducer 180 and increases in speed. Similarly, the second diameter D1 extends over a distance d2 such that the cold slurry travels this distance through the second passageway 175 before it exits the cold slurry syringe 100. In another example, an angle made between the longitudinal axis LA and an interior wall of the third passageway 185 (denoted in the figure as A) can be between 0 and 90 degrees. Preferably the angle is between about 10 and about 80 degrees and more preferably between about 20 and 70 degrees.

The syringe head 155 can include features for improving the flow of cold slurry. For example in FIG. 2C, the syringe head 155 includes projections 190 extending from an interior wall of the third passageway 185 toward the longitudinal axis LA. Ice particles making up the cold slurry can aggregate together and form ice clumps that can clog the cold slurry syringe 100 and impede cold slurry delivery. As the cold slurry flows through the syringe head 155, the projections 190 break up the ice clumps and, thereby, reduce the likelihood of clogging the cold slurry syringe. It is also contemplated that other areas of the cold slurry syringe can be lined with projections to improve the flow of cold slurry.

The cold slurry syringe 100 also includes at least one needle 140 (not shown) extending from the outlet 165. The needle can have a thickness between 7 gauge and 34 gauge; and can have a length between ¼" and 10", such as about ¼", ½", 1", 2", 3", 4", 5", 6", 7", 8", 9", or 10". Preferably, the needle is a hypodermic needle. Exemplary needle materials include, but are not limited to, stainless steel and carbon steel, with or without nickel plating.

In a convenient example, the outlet 165 is configured to receive and engage the needle. For example, the outlet 165 and the needle are Luer lock connectors that twist together to make a Luer lock connection. In another example, the outlet 165 is a slip tip onto which the needle is connected. A cold slurry syringe with a slip tip outlet can be connected to tubing or other flexible conduit. In this case, cold slurry is delivered through the tubing.

In order for cold slurry to pass through the needle without clogging, the largest cross-section of the ice particles must be smaller than the internal diameter of the needle. For example, the largest cross section can be less than about 95% of the internal diameter, less than about 85% of the internal diameter, less than about 75% of the internal diameter, less than about 65% of the internal diameter, less than about 55%, and preferably about 50% of the internal diameter. Exemplary ice particle sizes for various internal diameters, as disclosed in International Patent Application No. PCT/US2015/047292, are provided below in Table 1. It is to be understood that these particles sizes are only meant to be exemplary and not for limitation.

| Needle Gauge | Nominal Internal Diameter | Recommended Largest Cross-Section of Ice Particles |
| --- | --- | --- |
| 7 | 3.81 mm | 1.905 mm |
| 8 | 3.429 mm | 1.7145 mm |
| 9 | 2.997 mm | 1.4985 mm |
| 10 | 2.692 mm | 1.346 mm |
| 11 | 2.388 mm | 1.194 mm |
| 12 | 2.159 mm | 1.0795 mm |
| 13 | 1.803 mm | 0.9015 mm |
| 14 | 1.6 mm | 0.8 mm |
| 15 | 1.372 mm | 0.686 mm |
| 16 | 1.194 mm | 0.597 mm |
| 17 | 1.067 mm | 0.5335 mm |
| 18 | 0.838 mm | 0.419 mm |
| 19 | 0.686 mm | 0.343 mm |
| 20 | 0.603 mm | 0.3015 mm |
| 21 | 0.514 mm | 0.257 mm |
| 22 | 0.413 mm | 0.2065 mm |
| 22s | 0.152 mm | 0.076 mm |
| 23 | 0.337 mm | 0.1685 mm |
| 24 | 0.311 mm | 0.1555 mm |
| 25 | 0.26 mm | 0.13 mm |
| 26 | 0.26 mm | 0.13 mm |
| 26s | 0.127 mm | 0.0635 mm |
| 27 | 0.21 mm | 0.105 mm |
| 28 | 0.184 mm | 0.092 mm |
| 29 | 0.184 mm | 0.092 mm |
| 30 | 0.159 mm | 0.0795 mm |
| 31 | 0.133 mm | 0.0665 mm |
| 32 | 0.108 mm | 0.054 mm |
| 33 | 0.108 mm | 0.054 mm |
| 34 | 0.0826 mm | 0.0413 mm |

Returning back to the cold slurry syringe 100, the plunger 120, including the stopper 122 and the stem 126, can be any type of biocompatible, pharmacologically inert material suitable for coming in contact with sterile substances to be provided within a human body. Exemplary materials for the plunger 120 include plastic, such as polyethylene or polypropylene, and glass. With respect to the stopper 122, a portion or all of the stopper 122 can be a rubber material, such that a seal is formed between the sides of the stopper 122 and the interior wall of the syringe body 110. The rubber material can be any rubber suitable for coming in contact with sterile substances to be provided to the human body, such as natural rubber latex or a synthetic rubber.

Figure 3A:
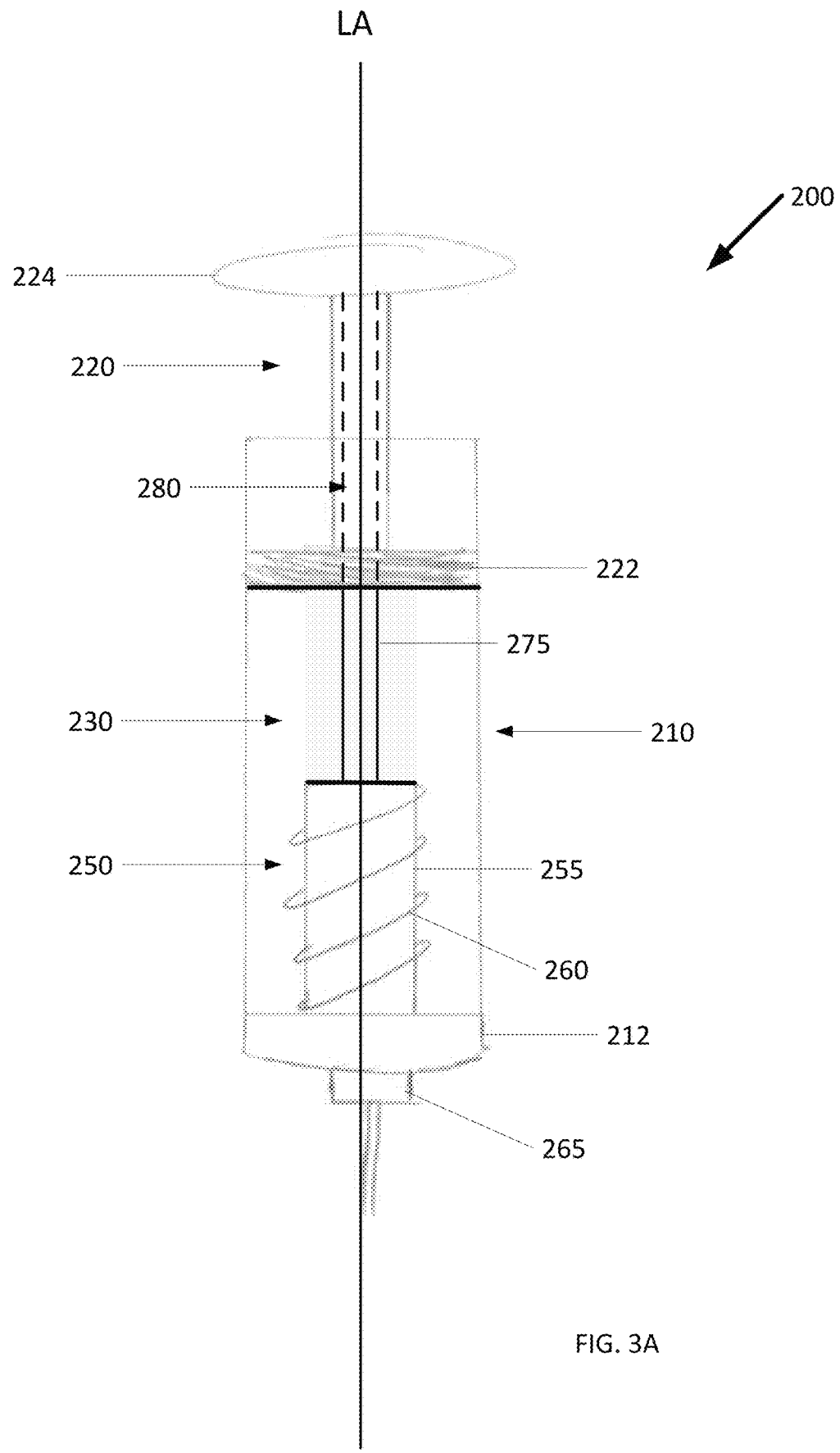
FIG. 3A is a cross section view of an example cold slurry syringe with an agitator.

To keep ice particles making up the cold slurry from aggregating, as the cold slurry is contained within a cold slurry syringe awaiting delivery, the cold slurry can be agitated. FIG. 3A shows an example cold slurry syringe 200 with an agitator 250 for stirring the cold slurry syringe and retarding the formation of ice clumps, which can clog the cold slurry syringe 200. The agitator 250 is housed within an interior lumen 230 between a plunger 220 and a first end 212 of a syringe body 210. The agitator 250 includes a hub 255 and a plurality of fins 260 radiating from the hub 255 towards the wall of the interior lumen 230.

As shown, the fins 260 extend out from the hub 255 along a plane that intersects longitudinal axis LA at an angle forming a spiral (or helical) pattern. Alternatively, the fins can extend out from the hub along a plane wherein one dimension of the plane is defined by the longitudinal axis. The agitator 250 can be made out of any material that is suitable for contact with sterile compositions to be delivered to the human body, including those exemplary materials previously provided with respect to the syringe body 110, plunger 120, and needle of FIGS. 2A-2C.

Figure 3C:
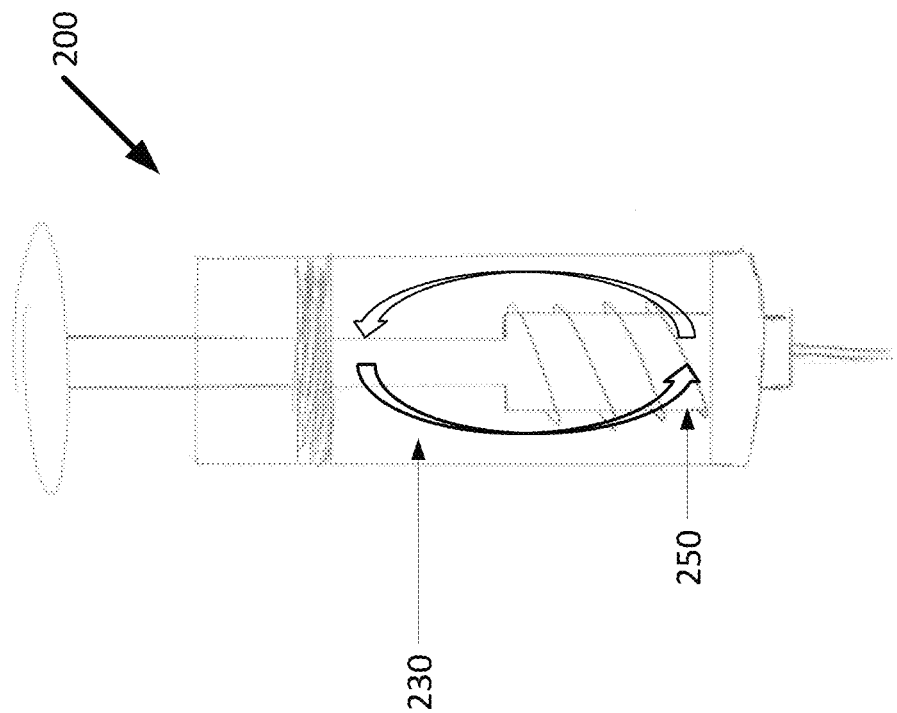
FIGS. 3B and 3C are views of the agitator circulating cold slurry within the cold slurry syringe.
Figure 3B:
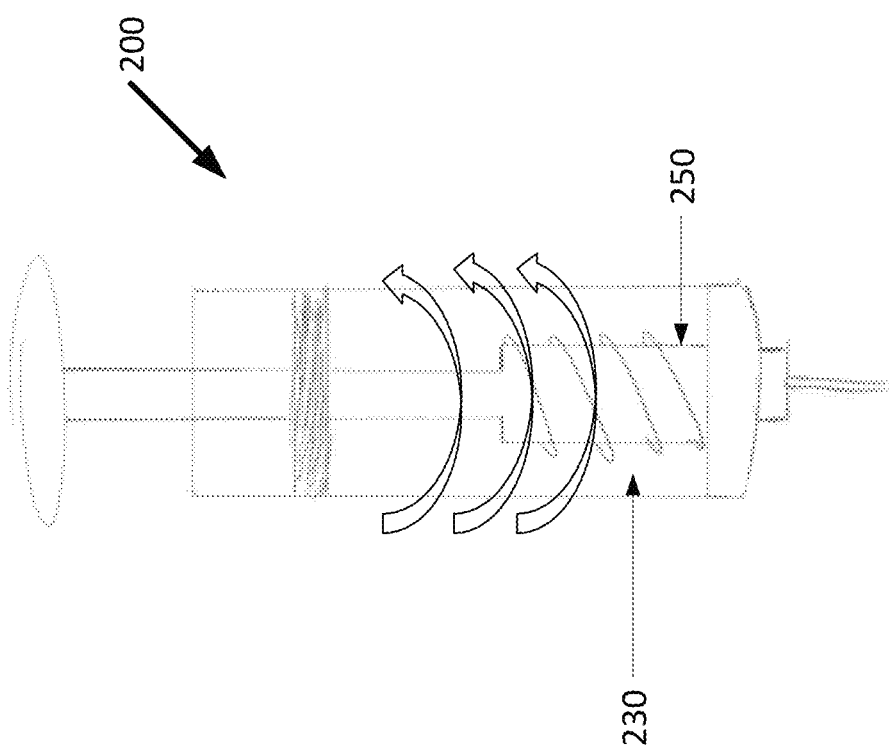

The agitator 250 includes a shaft 275 extending from the hub 255 and through a central bore 280 of the plunger 220. Rotating the shaft 275 turns the agitator 250, which in turn causes cold slurry to flow within the interior lumen 230 in multiple directions, as shown in FIGS. 3B and 3C. As shown, the shaft 275 terminates at a plunger head 224. In this example, the agitator 250 is turned manually by turning the plunger head 224 by hand or with a crank.

Figure 4B:
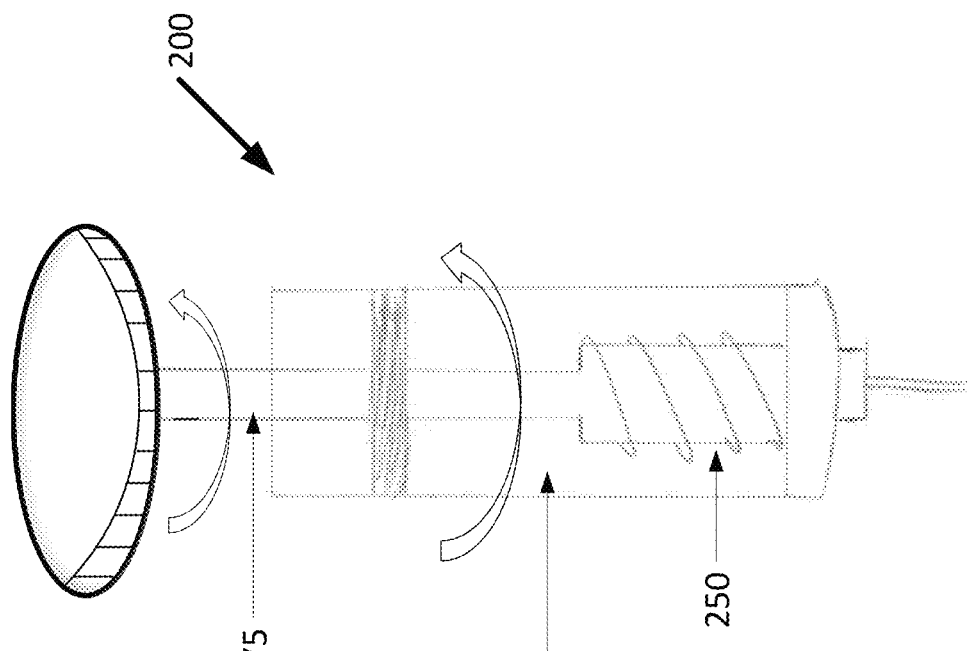
FIGS. 4A and 4B are views of different motor configurations for rotating the agitator.
Figure 4A:
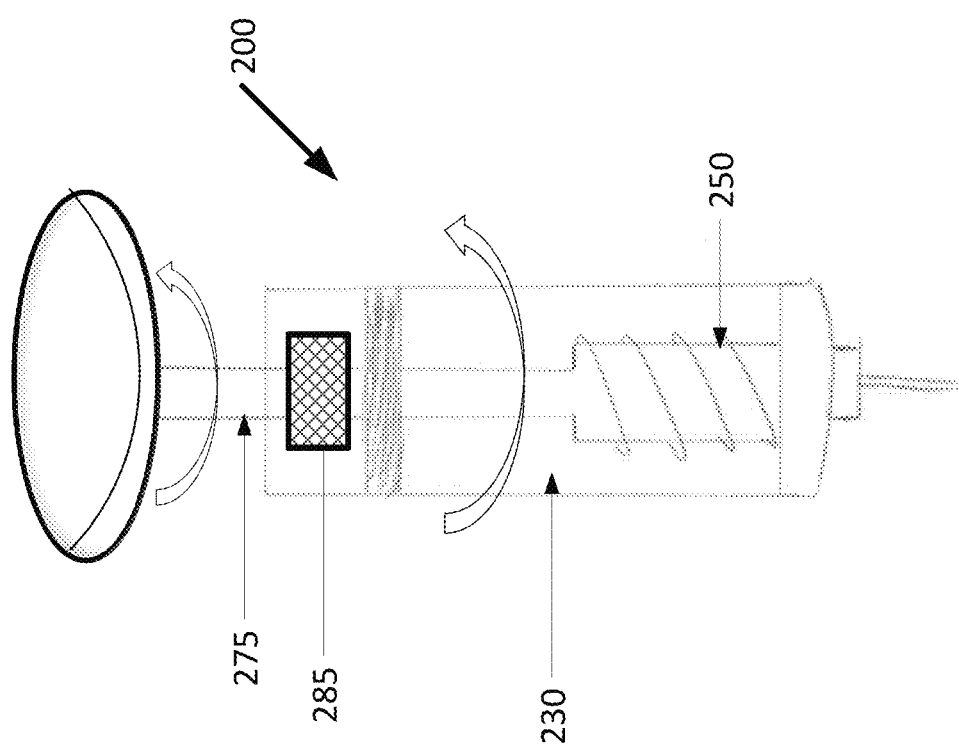

In another example, rotation of the agitator 250 is aided by the use of a motor 285. The motor 285 can be drivingly coupled to the cold slurry syringe 200 in any number of ways. For example, the motor 285 is directly coupled to the shaft 275, as shown in FIG. 4A, with the shaft 275 acting as a gear. In another example shown in FIG. 4B, the motor 285 is coupled to the plunger head 224 and the shaft 275 is fixed to the plunger head 224. In this case, the plunger head 224 acts a gear, which when driven by the motor (not shown), spins the agitator 250.

Figure 3D:
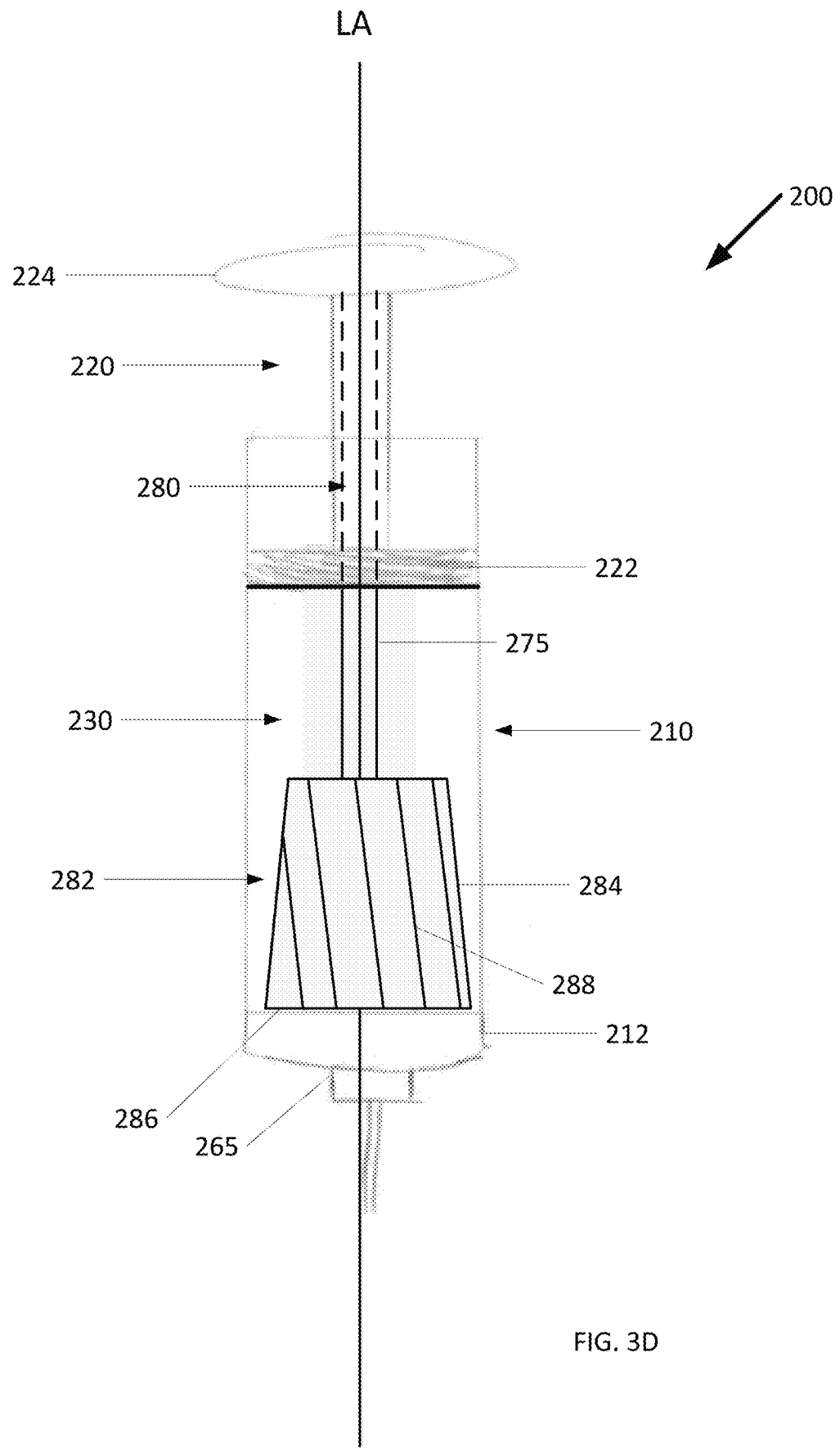
FIG. 3D is a view of another example cold slurry syringe with an agitator.

The agitator 250 can have a number of different configurations. For example, FIG. 3D shows an agitator 282 with a hub 284 shaped like a frustum of a cone. A base 286 of the hub 284 (i.e., wider end) faces the first end 212 of the syringe body 210. The hub 284 and fins 288 define a mixing profile. As shown, the mixing profile of the agitator 282 increases in the direction toward an outlet 265. Advantageously, this arrangement facilitates breaking up of ice clumps and improves the flow of cold slurry.

Referring back to FIG. 2A, to deliver cold slurry using the cold slurry syringe 100, for example, a clinician presses down on the plunger head 124, which in turn forces the plunger 120 downward towards the first end 112 of the syringe body 110. The force of the descending plunger 120 on the cold slurry, in conjunction with the increase in pressure of the cold slurry, forces the cold slurry out the syringe body and delivers the cold slurry. In this example, a linear motion is used to deliver the cold slurry. Other examples of the invention, convert a rotary motion to a linear motion for driving the plunger and delivering the cold slurry.

FIG. 5A shows the user end of an example syringe 300 in which a rotary motion is converted into a linear motion for delivering cold slurry. The syringe 300 includes a syringe body 305 having a first end (not shown) and an opposing second end 310. Extending away from the syringe body 305 from the second end 310 is a fixed screw 315 with threads 318.

The syringe 300 further includes a plunger 320 partially disposed within an interior lumen 307 containing a volume of cold slurry. The plunger 320 has a through bore 322 for receiving the screw 315 allowing the plunger 320 to rotate about the screw 315. The plunger 320 further includes a stopper 325 at one end and a plunger head 330 at an opposing end. A stem 335 extends between the stopper 325 and the plunger head 330 separating the two by a distance. The stem 335 further includes a nut 340 for engaging the screw threads 317. Rotating the plunger head 330 in a first direction moves the stopper 325 from the second end 310 to the first end. This in turn, pushes the cold slurry out of the interior lumen 307 and delivers the cold slurry to a target tissue. Rotating the plunger head 330 in a second direction moves the stopper 325 from the first end to the second end 310. This motion can be used to draw cold slurry into the interior lumen 307 from, for example, a cold slurry generator (an example of which is described in U.S. Provisional Application 62/416,484, which is incorporated herein in its entirety).

FIG. 5B shows the user end of another example cold slurry syringe 350 in which a rotary motion is converted into a linear motion for delivering cold slurry. The cold slurry syringe 350 includes a syringe body 355 having a first end (not shown) and an opposing second end 360. A nut 390 is fixed to the second end 360 of the syringe body 355.

The cold slurry syringe 350 further includes a plunger 370 partially disposed within an interior lumen 357 containing a volume of cold slurry. The plunger 370 includes a stopper 375 at one end and a plunger head 380 at an opposing end. A screw 385 extends between the stopper 375 and the plunger head 380 separating the two by a distance. The screw 385 further includes threads 387 for engaging the nut 390, which is fixed to the second end 360 of the syringe body 355. Rotating the plunger head 380 in a first direction moves the stopper 375 from the second end 360 to the first end. This in turn, pushes the cold slurry out of the interior lumen 357 and delivers the cold slurry to a target tissue. Rotating the plunger head 380 in a second direction moves the stopper 375 from the first end to the second end 360. This motion can be used to draw cold slurry into the interior lumen 357 from, for example, a cold slurry generator (an example of which is described in U.S. Provisional Application 62/416,484, which is incorporated herein in its entirety). Some examples of the cold slurry syringe 350 have a motor drivingly coupled to the plunger head 380, for example, by way of gears, belt and pulley or rack and pinion. The motor drives the head in the first direction to inject the cold slurry and drives the head on the second direction to withdraw the cold slurry. The motor, in turn, can be operable coupled to an electronic controller. Advantageously, with such a controller cold slurry can be injected or withdraw in an automated, autonomous or regulated fashion. The motor can be electrical DC or AC motor. Example motors include rotational and vibrational motors.

As shown in FIGS. 5A and 5B, the screw 315/385 can be a ball screw and the nut 340/390 can a ball nut that make up a ball screw drive. The ball nut is packaged as an assembly with recirculating ball bearings that roll in matching forms in the interface between the ball screw and the ball nut. With rolling elements, the ball screw drive has a very low coefficient of friction (on the order of u=0.01 to u=0.005), and is suitable for use with high precision and can apply/withstand high thrust loads. (In comparison, a conventional slide screw having similar a lead angle has a coefficient of friction on the order of u=0.1 and requires three times the driving torque.) A benefit to using the ball screw drive in the cold slurry syringe 300/350 is that it allows for a smooth and consistent application of pressure as cold slurry is ejected. The ability to withstand high thrust loads allows for the cold slurry to maintain a smooth, consistent force directed downwards and out of the cold slurry syringe 300/350, counteracting any opposing force to the system.

Another example of the cold slurry syringe includes a hydraulic piston for controlling the rate at which the cold slurry syringe is pressed and the cold slurry is ejected. The hydraulic piston is coupled to the plunger in order to maintain a constant and consistent pressure on the plunger throughout the closed system while plunging and delivering the cold slurry. In this mechanism, the hydraulic piston is mounted on top of the plunger, which with mechanical force, acts on a small cross-sectional area, displacing an incompressible fluid and displacing an equal volume of slurry at a constant rate from the syringe body. This process is performed in order to control possible changes in phase, temperature, and/or pressure on the slurry.

In general, to limit heat from transferring from the environment surrounding the cold slurry syringe to the cold slurry and melting the cold slurry, the cold slurry syringe can be surrounded in insulation. In one embodiment according to the present invention shown in FIG. 6A, an insulation 400 surrounds the syringe body 110 and maintains a temperature of the cold slurry within the interior lumen 130. As best seen in the cross section of FIG. 6B (with the plunger 120 omitted for clarity), the insulation 400 is concentric with an outer surface 111 of the syringe body 110.

Figure 6A:
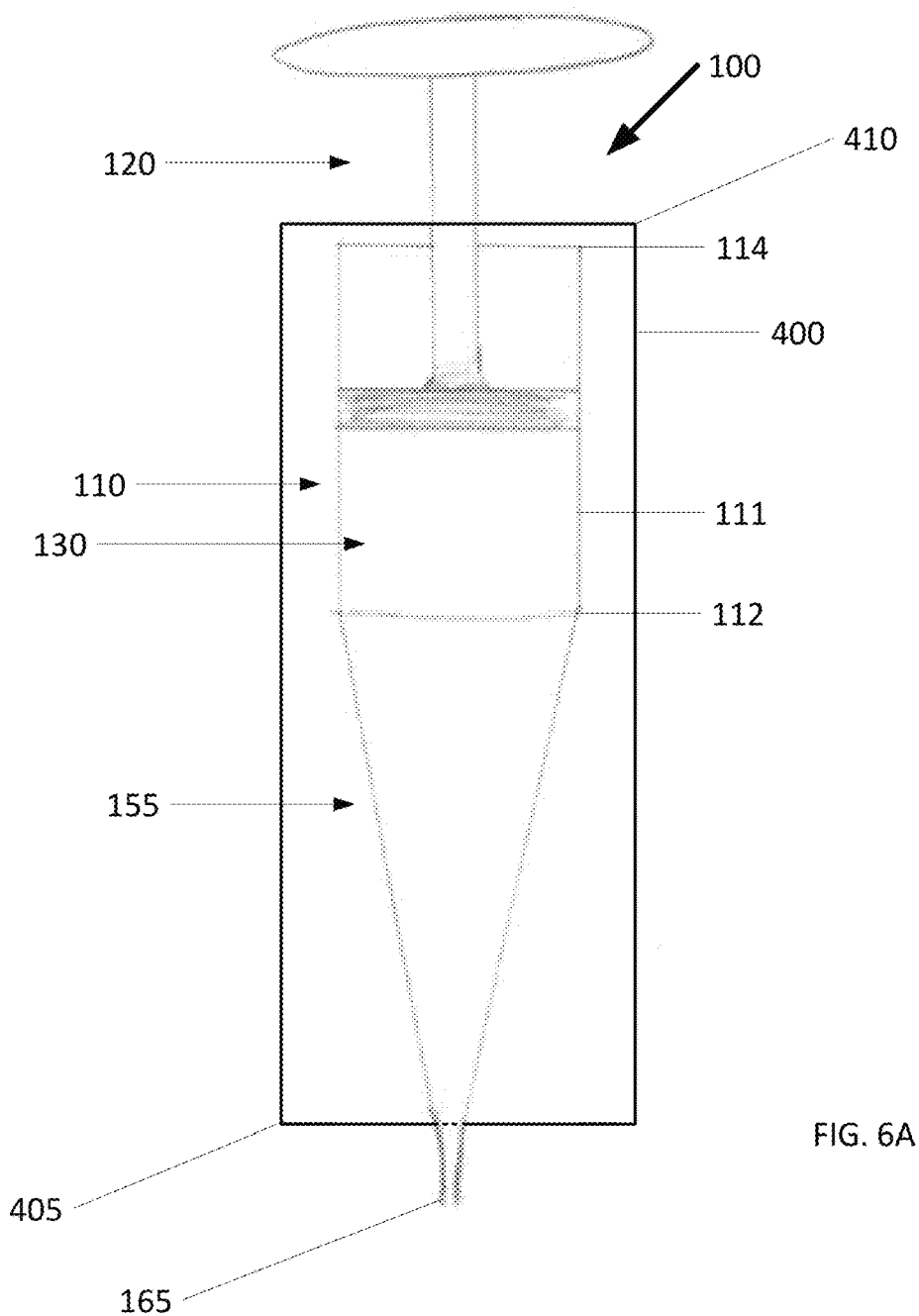
FIG. 6A is a view of a cold slurry syringe having insulation for limiting heat from transferring from the environment surrounding the cold slurry syringe to the cold slurry.
Figure 6B:
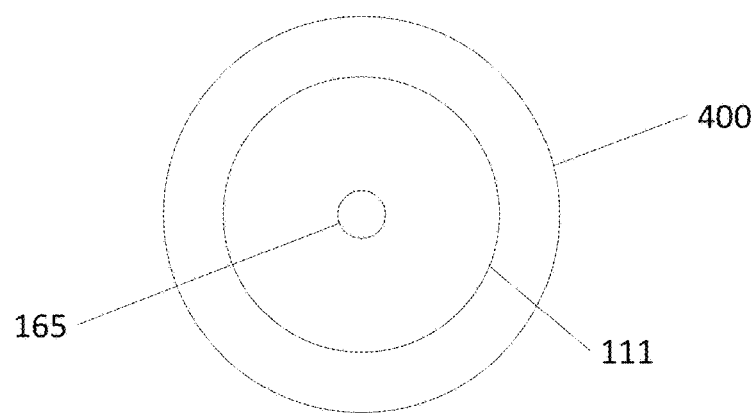
FIG. 6B is a cross section view of the cold slurry syringe with insulation of FIG. 6A.

As shown in FIG. 6A, the insulation 400 extends past the first end 112 of the syringe body 110 towards the outlet 165 at its bottom 405. The insulation 400 extends past the second end 114 of the syringe body 110 towards the plunger head 124 at its top 410. As such, the insulation 400 substantially encompasses the cold slurry syringe 100. Alternatively, the insulation 400 can surround the syringe body 110 with the bottom 405 ending at or near the first end 112 and the top 410 ending at or near the second end 114.

In a convenient example, the insulation 400 is an insulation sleeve for receiving the cold slurry syringe 100. The insulation sleeve can have an open end through which the cold slurry syringe 100 is loaded. A removable cap can further be provided at the open end to allow for insertion and subsequent enclosure of the cold slurry syringe 100 within the insulation sleeve. In another example, the insulation sleeve is of a clamshell design with two halves.

The insulation 400 can be made out of fiberglass insulation, foam insulation, gel insulation, and aerogel insulation, just to name a few examples. The insulation 400 can also be rigid insulation so that when pressure is exerted on the cold slurry syringe (e.g., when delivering cold slurry), the syringe body does not expand or change shape. Similar to the components of the cold slurry syringe, the insulation 400 can also be made out of any material that is biocompatible and pharmacologically inert.

Figure 7B:
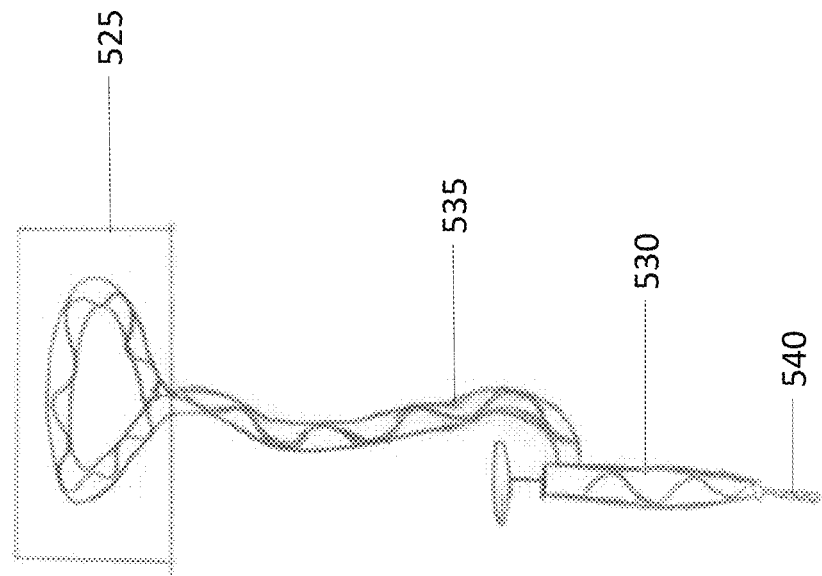
FIG. 7B is a view of devices for generating and delivering cold slurry that incorporate the streamline flow feature.
Figure 7A:
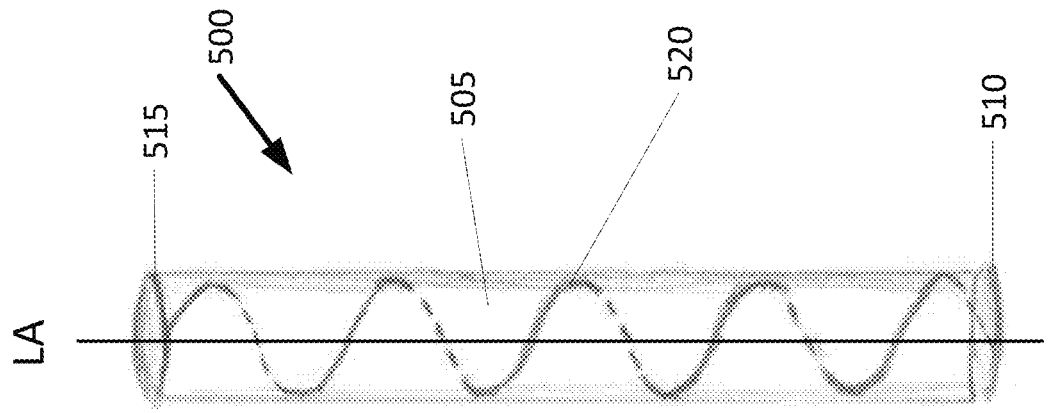
FIG. 7A is a view of an example of a streamline flow feature.

A streamline flow feature can be used to maintain velocity, pressure, and other properties of cold slurry flow from when the cold slurry is generated to when the cold slurry is injected. FIG. 7A shows an example of the streamline flow feature 500 having a core structure 505 that extends between a first end 510 and a second end 515. The core structure 505 defines a passageway 520 through which cold slurry flows.

The passageway 520 extends along a longitudinal axis LA between the first end 510 and the second end 515 with a plane of the passageway 520 intersecting the longitudinal axis LA at an angle forming a spiral (or helical) pattern. Because of this arrangement, cold slurry can flow throw through the streamline flow feature 500 without turbulence, in parallel layers with no disruption between the layers, and with no cross-currents perpendicular to the flow direction. The streamline flow feature 500 can also reduce the occurrence of eddies or swirls.

Cold slurry moves through the streamline flow feature 500 as a laminar flow allowing ice particles to move parallel to the passageway surface. This can help maintain cold slurry composition (e.g. ice content) from when the cold slurry is generated to when the cold slurry is injected in a patient. It can further help reduce agglomeration and/or inconsistency in cold slurry composition. FIG. 7B shows the streamline flow feature used in devices for generating and delivering cold slurry, including a cold slurry generator 525 (of which only an internal component is shown), a cold slurry syringe 530, tubing 535 for transferring cold slurry from the cold slurry generator 525 to the cold slurry syringe 530, and a needle 540 for piercing the patient's skin and delivering cold slurry to a target tissue.

The cold slurry syringes 100, 200, 300, 350, and 530 described above can be used to deliver a wide variety of cold slurries. For example, the cold slurry can have a temperature of about 10° C., 7° C., 5° C., 4° C., 3° C., 2° C., 1° C., 0° C., −1° C., −2° C., −3° C., −4° C., −5° C., −10° C., −15° C., −20° C., −30° C., −40° C., and −50° C. The cold slurry can contain between about 0.1% and about 75% ice by weight, between about 0.1% and 1% ice by weight, between about 1% and 10% ice by weight, between about 10% and about 20% ice by weight, between about 20% and about 30% ice by weight, between about 30% and about 40% ice by weight, between about 40% and about 50% ice by weight, between about 50% and about 60% ice by weight, between about 60% and about 70% ice by weight, and greater than about 50% ice by weight. (The proportions of ice by volume are slightly higher due to the densities of solid and liquid water.) The cold slurry can include ice particles having a largest cross-sectional dimension that is less than about 2 mm, about 1.75 mm, about 1.5 mm, about 1.25 mm, about 1 mm, about 0.9 mm, about 0.8 mm, about 0.7 mm, about 0.6 mm, about 0.5 mm, about 0.4 mm, about 0.3 mm, about 0.2 mm, or about 0.1 mm. Other exemplary cold slurry compositions, slurry temperatures, and cross-sectional dimensions of ice particles are provided in PCT/US2015/047292, which is incorporated herein in its entirety. It is to be understood that an advantage of the cold slurry in accordance with the present invention is that the composition of the cold slurry is suitable to delivery to tissues within the body, such that the slurry can be delivered to a tissue within the body of a patient and remain within the body (e.g. no removal of the slurry is necessary after cooling has been effected).

EQUIVALENTS

While the present invention has been described in conjunction with certain preferred embodiments, one of ordinary skill, after reading the foregoing specification, will be able to effect various changes, substitutions of equivalents, and other alterations to the apparatuses and methods set forth herein.

The invention claimed is:

1. A device for delivering cold slurry, the device comprising:
 a syringe body comprising:
  a first end and a second end;
  a longitudinal axis extending from the first and second ends;
  an interior lumen defined by an interior wall of the syringe body, the interior lumen configured to receive and contain a volume of cold slurry;
 a plunger slideably movable within the interior lumen along the longitudinal axis, the plunger comprising a stopper and a stem extending from the stopper;
 a syringe head extending from the first end of the syringe body along the longitudinal axis, the syringe head comprising:
  an inlet defining a first passageway in fluid communication with the interior lumen of the syringe body, the first passageway having a first diameter about the same as a diameter of the interior lumen;
  an outlet spaced a predetermined distance from the inlet along the longitudinal axis, the outlet defining a second passageway in fluid communication with outside to serve as an exit for delivering cold slurry, the second passageway having a second diameter smaller than the first diameter; and
  a reducer extending between the inlet and outlet, the reducer defining a third passageway in fluid communication with the first and second passageways, the third passageway having a third diameter tapering from the first diameter to the second diameter; and
 an agitator for stirring the cold slurry within the interior lumen, the agitator housed within the interior lumen and interposed between the plunger and the first end of the syringe body, the agitator comprising:
  a hub shaped as a frustum of a cone with a base facing the first end of the syringe body; and
  a plurality of fins radiating from the hub towards the interior wall of the syringe body.

2. The device of claim 1, wherein the third passageway includes at least one projection extending inwardly towards to the longitudinal axis to agitate the cold slurry as the cold slurry is being delivered from the device.

3. The device of claim 1, wherein the second passageway is a slip tip for receiving tubing.

4. The device of claim 1, wherein the plurality of fins are arranged in a spiral pattern around the hub.

5. The device of claim 1, wherein the plunger includes a central bore; and
 wherein the agitator includes a shaft extending through the central bore of the plunger, the shaft for rotating the agitator and stirring the cold slurry within the interior lumen.

6. The device of claim 5, wherein the agitator includes a motor coupled to the shaft for stirring the cold slurry within the interior lumen, mechanically.

7. The device of claim 5, wherein the agitator includes a plunger head coupled to the shaft for stirring the cold slurry within the interior lumen, manually.

8. The device of claim 1 further comprising an insulation surrounding the syringe body to maintain a temperature of the cold slurry within the interior lumen.

9. The device of claim 8, wherein the insulation is any one of fiberglass insulation, foam insulation, gel insulation, and aerogel insulation.

10. The device of claim 8, wherein the insulation is an insulating sleeve for receiving the syringe body.

11. The device of claim 1 further comprising a ball screw fixed to and extending away from the second end of the syringe body;
 wherein the plunger includes a through bore for rotating the plunger about the ball screw;
 wherein the plunger further includes a plunger head at an end opposite the stopper;
 wherein the stem includes a ball nut located between the plunger head and the stopper; and wherein the ball nut threadedly engages the ball screw such that turning the plunger head moves the stopper between the first end to the second end of the syringe body.

12. The device of claim 1, wherein the stem is a ball screw with a plunger head at an end opposite the stopper, and the device further comprising a ball nut fixed to the second end of the syringe body; and wherein the ball nut threadedly engages the ball screw such that turning the plunger head moves the stopper between the first end to the second end of the syringe body.

13. The device of claim 1 wherein the interior lumen is a streamline flow feature comprising a core structure and a passageway defined by the core structure;

wherein a plane of the passageway intersects the longitudinal axis at an angle.

14. The device of claim 1, wherein the syringe body is made any one of polyethylene, polypropylene, and glass.

15. The device of claim 1, wherein the interior lumen receives a volume of cool fluid that changes to the volume of cold slurry.

16. The device of claim 1, wherein the reducer has a conical shape.

* * * * *

UNITED STATES PATENT AND TRADEMARK OFFICE
CERTIFICATE OF CORRECTION

| | | |
|---|---|---|
| PATENT NO. | : 10,500,342 B2 | Page 1 of 1 |
| APPLICATION NO. | : 15/682234 | |
| DATED | : December 10, 2019 | |
| INVENTOR(S) | : Christopher Velis | |

It is certified that error appears in the above-identified patent and that said Letters Patent is hereby corrected as shown below:

On the Title Page

Item (72): "Christopher J.P. Velis" should be -- Christopher Velis --.

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*